United States Patent
Malin

(10) Patent No.: US 9,784,495 B2
(45) Date of Patent: Oct. 10, 2017

(54) STORAGE CASSETTE FOR LABORATORY OBJECTS

(75) Inventor: Cosmas G. Malin, Mauren (LI)

(73) Assignee: LICONIC AG, Mauren (LI)

(*) Notice: Subject to any disclaimer, the term of this patent is extended or adjusted under 35 U.S.C. 154(b) by 947 days.

(21) Appl. No.: 13/304,098

(22) Filed: Nov. 23, 2011

(65) Prior Publication Data

US 2012/0134897 A1    May 31, 2012

(30) Foreign Application Priority Data

Nov. 24, 2010    (CH) ........................................ 1968/10

(51) Int. Cl.
| | |
|---|---|
| *B01L 1/00* | (2006.01) |
| *B01L 9/00* | (2006.01) |
| *F25D 25/00* | (2006.01) |
| *G01N 35/00* | (2006.01) |
| *G01N 35/02* | (2006.01) |
| *F25D 13/04* | (2006.01) |
| *F25D 13/06* | (2006.01) |
| *F25D 3/10* | (2006.01) |
| *G01N 35/04* | (2006.01) |

(52) U.S. Cl.
CPC ............. *F25D 25/005* (2013.01); *F25D 3/10* (2013.01); *F25D 13/04* (2013.01); *F25D 13/06* (2013.01); *G01N 35/0099* (2013.01); *G01N 35/028* (2013.01); *G01N 2035/00445* (2013.01); *G01N 2035/0425* (2013.01)

(58) Field of Classification Search
CPC .................................................... F25D 25/005
See application file for complete search history.

(56) References Cited

U.S. PATENT DOCUMENTS

| | | |
|---|---|---|
| 4,250,266 A | 2/1981 | Wade |
| 4,771,900 A | 9/1988 | Leoncavallo et al. |
| 4,832,195 A * | 5/1989 | Dahl ........................ 206/387.15 |

(Continued)

FOREIGN PATENT DOCUMENTS

| | | |
|---|---|---|
| EP | 1 718 545 B1 | 1/2009 |
| WO | 97/483089 A1 | 12/1997 |

(Continued)

OTHER PUBLICATIONS

Austrian Search Report conducted in counterpart Austrian Appln. No. CH 1968/10.

(Continued)

*Primary Examiner* — P. Kathryn Wright
(74) *Attorney, Agent, or Firm* — Greenblum & Bernstein, P.L.C.

(57) ABSTRACT

A storage arrangement (1) has a chamber (3). Several Dewar flasks (5) are arranged in the chamber (3) and above them a picking device (8). The picking device has at least one cassette lift (60), with which storage cassettes (20) can be removed from above from the Dewar flasks (5). This arrangement is suitable for storing laboratory objects even at very low temperatures. Each storage cassette (20) is preferably made from a single piece of sheet metal. The piece of sheet metal is bent such that it forms the side walls (30), the back wall (32), the top part (34) and the base part (38) of the storage cassette (20), as well as angles (40, 42) to accommodate the laboratory objects.

9 Claims, 11 Drawing Sheets

(56) References Cited

U.S. PATENT DOCUMENTS

| | | |
|---|---|---|
| 4,907,889 A | 3/1990 | Simone |
| 5,192,506 A | 3/1993 | Kureshy et al. |
| 5,226,715 A | 7/1993 | Delatte |
| 5,233,844 A | 8/1993 | Knippscheer et al. |
| 5,266,272 A | 11/1993 | Griner et al. |
| 5,345,395 A | 9/1994 | Griner |
| 5,645,800 A | 7/1997 | Masterson et al. |
| 5,735,587 A | 4/1998 | Malin et al. |
| 6,129,428 A | 10/2000 | Helwig et al. |
| 6,478,524 B1 | 11/2002 | Malin |
| 6,568,770 B2 | 5/2003 | Gonska et al. |
| 6,881,572 B2 | 4/2005 | Fitzgerald et al. |
| 2001/0043031 A1 | 11/2001 | Gonska et al. |
| 2002/0063077 A1 | 5/2002 | Ferger et al. |
| 2004/0115101 A1 | 6/2004 | Malin |
| 2006/0006774 A1 | 1/2006 | Jackson et al. |
| 2006/0150659 A1 | 7/2006 | Sidor et al. |
| 2008/0180842 A1 | 7/2008 | Kaufmann et al. |
| 2008/0231152 A1 | 9/2008 | Malin |
| 2008/0260511 A1 | 10/2008 | Fattinger et al. |
| 2008/0272674 A1 | 11/2008 | Malin |
| 2009/0026905 A1 | 1/2009 | Malin |
| 2009/0090685 A1 | 4/2009 | Kristensen |
| 2009/0140616 A1 | 6/2009 | Fox |
| 2010/0183408 A1 | 7/2010 | Malin |
| 2010/0275636 A1 | 11/2010 | Yoshimura et al. |

FOREIGN PATENT DOCUMENTS

| | | | |
|---|---|---|---|
| WO | WO-97/48309 | * | 12/1997 |
| WO | 01/83694 A2 | | 11/2001 |
| WO | 02/059251 A2 | | 8/2002 |

OTHER PUBLICATIONS

Europe Search Report/Office Action conducted in counterpart Europe Appln. No. EP 11 00 9209 (w/ Partial English translation).

* cited by examiner

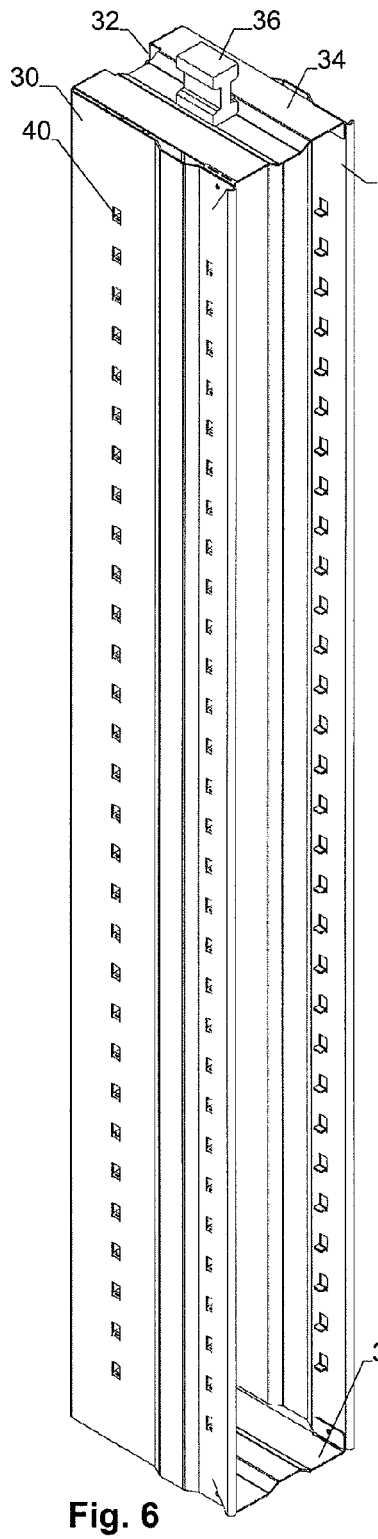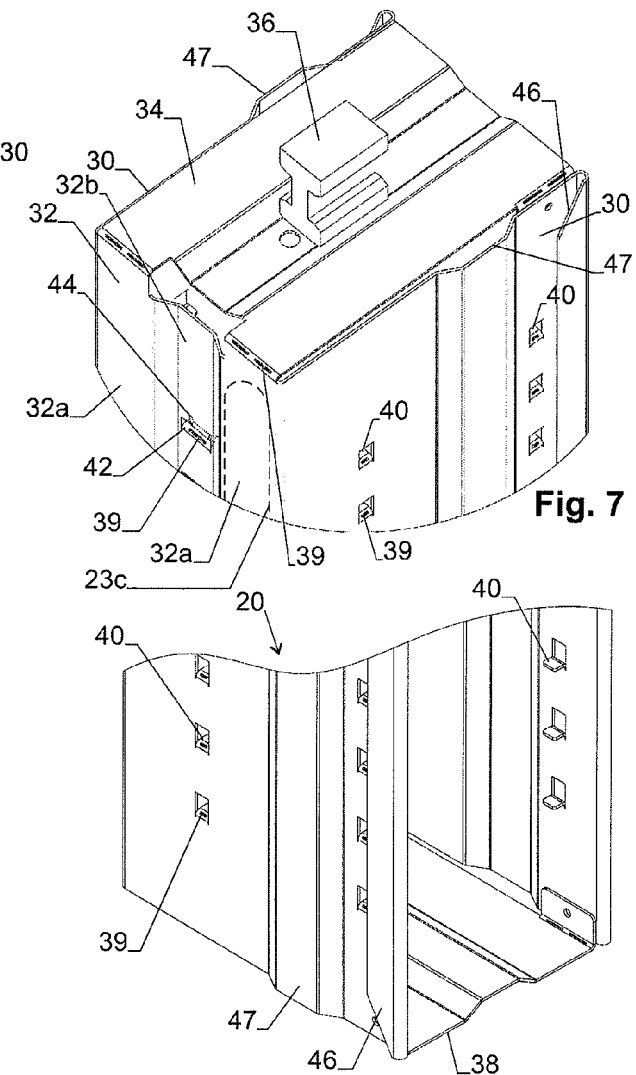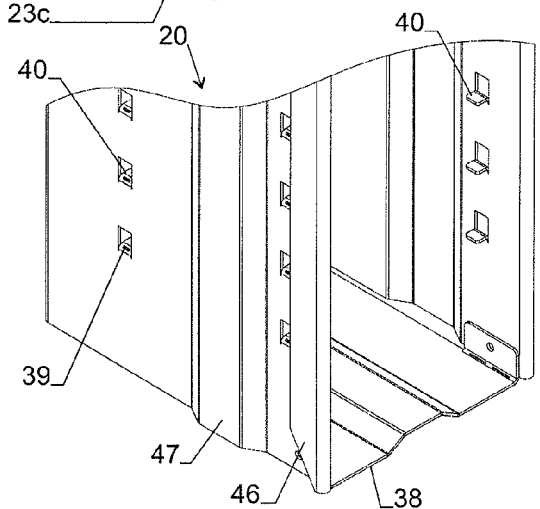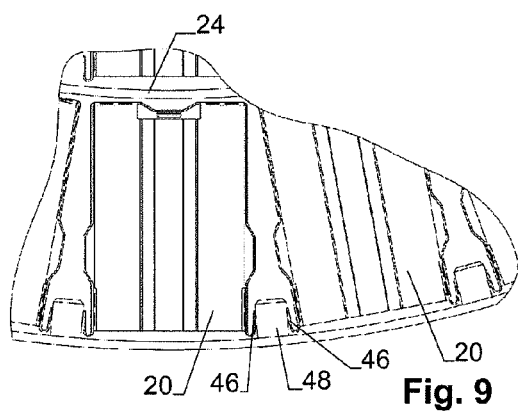
Fig. 6
Fig. 7
Fig. 8
Fig. 9

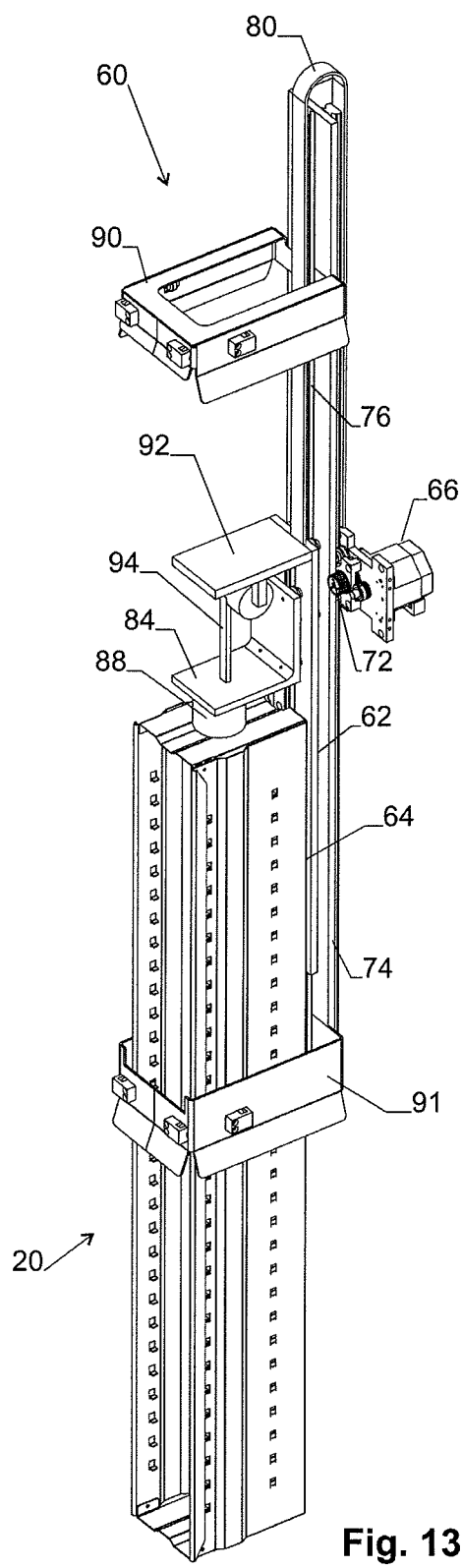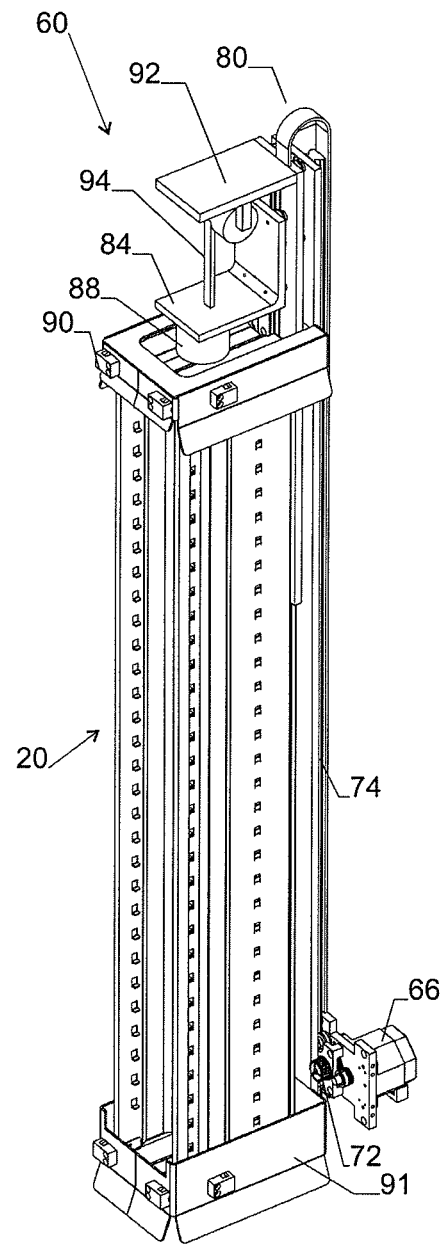
Fig. 13
Fig. 14

STORAGE CASSETTE FOR LABORATORY OBJECTS

CROSS-REFERENCE TO RELATED APPLICATIONS

The present application claims priority under 35 U.S.C. §119 of Swiss Patent Application No. CH-1968/10, filed Nov. 24, 2010, the disclosure of which is expressly incorporated by reference herein in its entirety.

BACKGROUND OF THE INVENTION

Field of the Invention

The invention relates to a storage cassette for laboratory objects, in particular for storage at low temperatures. Furthermore, the invention also relates to a storage arrangement with a storage cassette of this type as well as the combination of a storage cassette with at least one laboratory object.

Discussion of Background Information

Storage cassettes for laboratory objects, which form a plurality of storage sites arranged one above the other to accommodate the laboratory objects, are known, e.g., from WO 02/059251. When storage cassettes of this type are required in a large number, it should be ensured that they can be produced as easily and inexpensively as possible.

SUMMARY OF THE EMBODIMENTS

The present invention provides a storage cassette, which forms a plurality of storage sites arranged one above the other to accommodate laboratory objects, which can be produced in an inexpensive, tough and simple manner.

Accordingly, the storage cassette for laboratory objects according to the embodiments of the invention form a plurality of storage sites arranged one above the other to accommodate laboratory objects. The storage cassette includes a back wall and two side walls standing perpendicular to the back wall. The side walls and the back wall are formed by sections of a single piece of sheet metal bent towards one another.

Accordingly, the storage cassette has a back wall and two side walls standing perpendicular to the back wall. The side walls and the back wall are thereby formed by sections of a single piece of sheet metal bent towards one another. A storage cassette of this type can be produced easily and is tough due to the small number of parts used.

Furthermore, a top part or base part can be arranged on an upper and/or lower end of the storage cassette, which part is advantageously likewise formed by a bent section of the same piece of sheet metal. The strength of the cassette is further increased thereby and the price is reduced.

The storage sites of the storage cassette can be formed by bent angles of the piece of sheet metal, on which the laboratory objects can be placed. The angles can thus also be shaped from the same sheet metal as the back walls.

The angles on the back wall advantageously have retention elements bent upwards on their front edge in order to hold the laboratory objects secure against slipping.

Advantageously, predetermined bending locations are provided in the piece of sheet metal in order to facilitate the locally precise bending of the same. These predetermined bending locations are preferably formed in the shape of elongated holes or slots, which can be made in the same step as the cutting of the piece of sheet metal and thus in a well-defined spatial position.

The invention also relates to a storage arrangement with at least one chamber and at least one storage cassette of the type described above arranged in the chamber.

Embodiments of the invention are directed to a storage cassette for laboratory objects, which forms a plurality of storage sites arranged one above the other to accommodate laboratory objects. The storage cassette includes a back wall and two side walls standing perpendicular to the back wall. The side walls and the back wall are formed by sections of a single piece of sheet metal bent towards one another.

According to embodiments of the instant invention, the storage cassette can further include at least one of a top part and base part is arranged on a respective at least one of an upper and lower end of the storage cassette, and the at least one top and base part is formed by a bent section of the piece of sheet metal.

In accordance with other embodiments bent angle brackets can be formed on the piece of sheet metal that can be arranged as storage sites on which the laboratory objects may be placed. At least one of the angle brackets may be arranged on the back wall and provided with upwardly bent front edge retention elements structured and arranged to securely hold the laboratory objects against slipping.

According to further embodiments, predetermined bending locations may be arranged in the piece of sheet metal in the form of at least one of elongated holes and slots.

Further, the side walls can be structured and arranged to form bent over regions on a front side of the storage cassette.

Moreover, a first region of the back wall can form a spacer for the laboratory objects that delimits at least one second region of the back wall that may be recessed or set back.

In other embodiments of the invention, a steel or iron plate may be located at an upper end of the storage cassette.

In accordance with still further embodiments, at least two storage elements may be formed on each side wall for each storage site, and the at least two storage elements can be arranged such that:

$$|L/2-A|<B,$$

in which L is a length of the storage site, A is a distance of the at least two support elements and B is a length of one of the support elements. Moreover, the at least two storage elements can include angle brackets formed from the side walls.

Still other embodiments of the instant invention can be directed to a combination of the above-described storage cassette and at least one laboratory object, such that the combination includes at least two storage elements formed on each side wall for each storage site, and the at least two storage elements can be arranged such that:

$$|L/2-A|<B,$$

in which L is a length of the laboratory object, A is a distance of the at least two support elements and B is a length of one of the support elements. Also, the at least two storage elements may include angle brackets formed from the side walls.

Embodiments of the invention are directed to a storage arrangement that includes at least one chamber and at least one storage cassette, as described above, being arranged in the chamber. Further, at least one extendible scoop may be structured and arranged to at least one of retrieve and place a laboratory object. Moreover, the at least one extendible scoop can include at least one holder element structured and arranged to seize the laboratory object from behind, and the back wall of the storage cassette may include a first region forming a spacer for the laboratory objects and delimiting at least one second region of the back wall as a recess or set back area structured to receive the at least one holder element when retrieving or placing the laboratory object.

Embodiments of the invention are directed to a method of forming a storage cassette for laboratory objects. The storage cassette has a plurality of storage sites arranged one above the other to accommodate laboratory objects, and the method includes bending a single piece of sheet metal to form a back wall and two side walls arranged perpendicular to the back wall to form a storage cassette for laboratory objects, and forming bent angle brackets from the single piece of sheet steel in at least one of the back wall and the two side walls as storage sites on which the laboratory objects are positionable.

According to embodiments of the invention, the method can also include bending the single piece of sheet metal to form at least one of a top part and a base part on a respective at least one of an upper and lower end of the storage cassette.

Moreover, the method can also include forming bent angle brackets on the piece of sheet metal that are arranged as storage sites on which the laboratory objects are placed.

According to still other embodiments, the method may include bending the back wall to form a first region as a spacer for the laboratory objects that delimits at least one second region of the back wall that is recessed or set back.

In accordance with still yet other embodiments of the present invention, at least two angle brackets may be formed on each side wall to delimit each storage site, and the at least two storage elements can be arranged such that:

$$|L/2-A|<B,$$

such that L is a length of the storage site, A is a distance of the at least two support elements and B is a length of one of the support elements.

BRIEF DESCRIPTION OF THE DRAWINGS

Further embodiments, advantages and applications of the invention are shown by the dependent claims and from the following description based on the figures. They show:

FIG. 6 A storage cassette;

FIG. 7 The upper end of the storage cassette from FIG. 6;

FIG. 8 The lower end of the storage cassette from FIG. 6;

FIG. 9 The arrangement of storage cassettes in a Dewar flask;

FIG. 13 The cassette lift from FIG. 12 in center position;

FIG. 14 The cassette lift from FIG. 12 in the raised position;

DETAILED DESCRIPTION OF THE EMBODIMENTS

Figure 1:
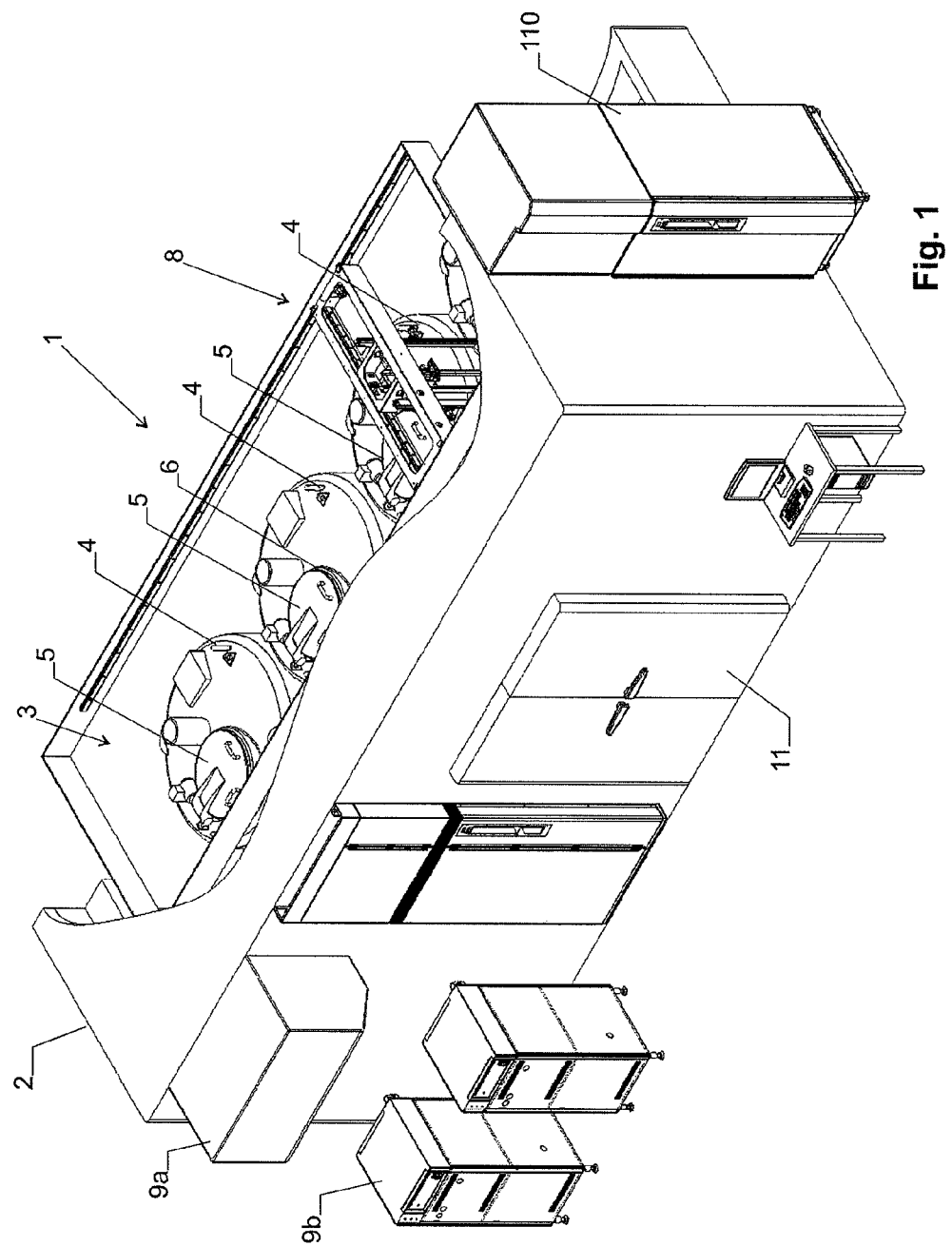
FIG. 1 A view of a storage arrangement, wherein the outer walls are shown only in part.
Figure 2:
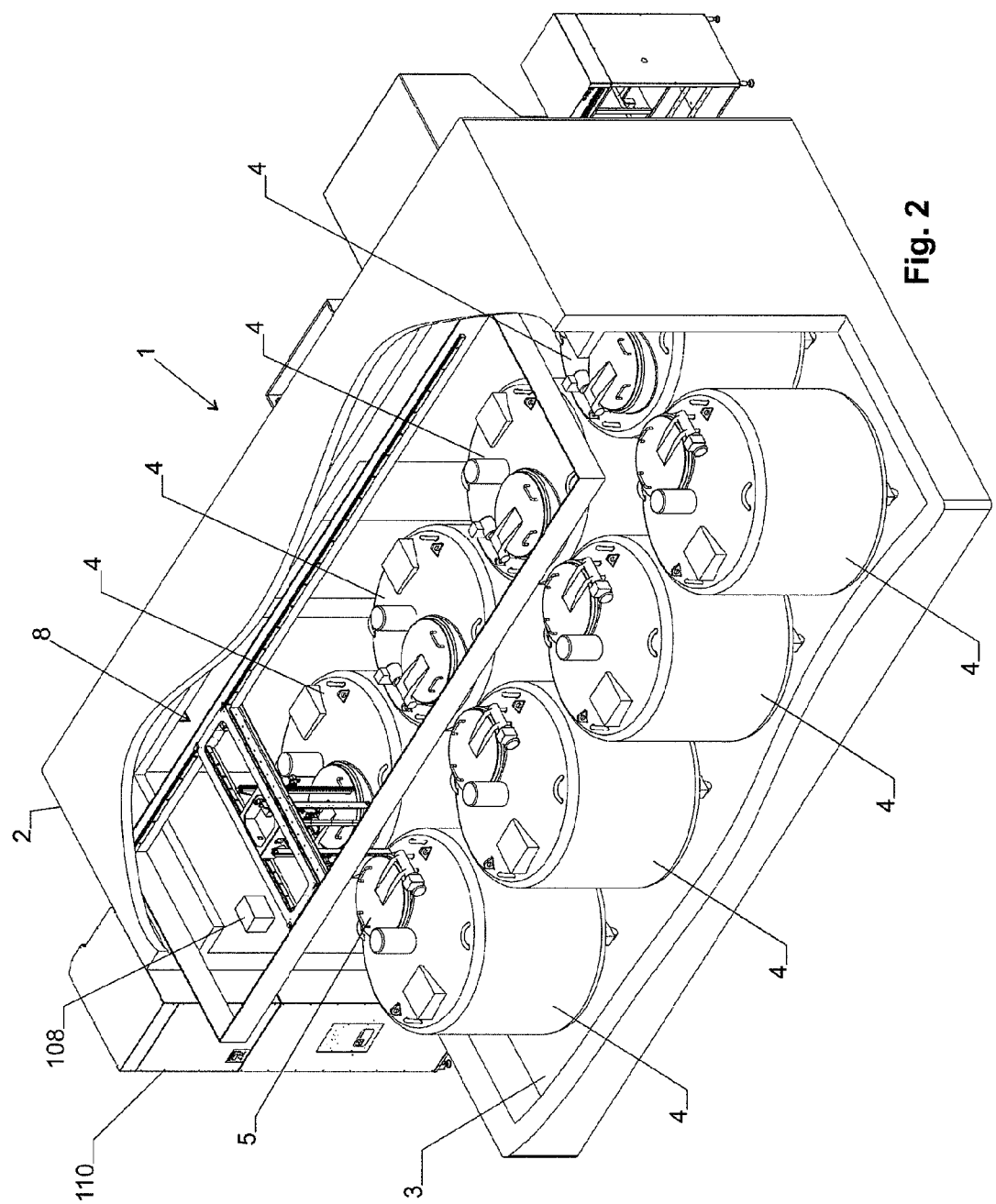
FIG. 2 A second view of the storage arrangement from FIG. 1.

Storage Arrangement:

FIGS. 1 and 2 show a storage arrangement 1 for the long-term storage of samples at very low temperatures, in particular a storage temperature Ts below 160° C., typically at −196° C. The storage arrangement is designed to deposit and retrieve the samples automatically and to move them inside the storage arrangement between different storage positions. Arrangements of this type have to meet high demands regarding safety for the samples, reliability and energy efficiency.

For example, the samples are accommodated in sample tubes, which in turn are arranged in plates. In each case several of these sample plates are stored one above the other in a storage cassette.

The storage arrangement has an insulated outer housing 2, which surrounds a chamber 3. At least one Dewar flask 4 is arranged in the chamber 3. Preferably, several of such Dewar flasks 4 are provided. Each Dewar flask 4 has in a known manner an evacuated, mirrored insulation wall, which has low thermal conductivity. The Dewar flasks 4 in the embodiment shown are closed on all sides and a lid 5 is respectively provided for access to their interior.

The lid 5 covers an opening 6 arranged on the top of the Dewar flask 4.

The chamber 3 is preferably embodied as a cooling chamber. Tc of the chamber 3 is preferably below 0° C., in particular below −20° C. or −50° C. This reduction of the temperature prevents ice formation in the Dewar flasks 4 or on the samples. The storage temperature Ts in the Dewar flasks 4 is less than the chamber temperature Tc and is preferably at the referenced "very low temperatures," i.e., typically at −196° C.

A cooling of the chamber 3 is not absolutely necessary however. The chamber 3 can also e.g., merely contain a defined atmosphere (for example dry air or nitrogen atmosphere), or it can be a storage area that is not specially air-conditioned.

Furthermore, a picking device 8 is arranged in the chamber 3. This picking device 8 has respectively one transport device for the storage cassettes, the sample plates and the sample tubes. It is arranged in a moveable manner above the Dewar flasks 4. As can be seen from FIGS. 1 and 2, advantageously exactly one picking device 8 is provided, which serves all of the Dewar flasks 4.

The storage arrangement further comprises a first cooling device 9a for producing the interior temperature Ti in the chamber 3 as well as a second cooling device 9b for producing the cooling temperature Ts in the Dewar flasks 4.

The chamber 3 can be accessed via a door 11, which is large enough to accommodate the Dewar flasks 4.

Figure 3:
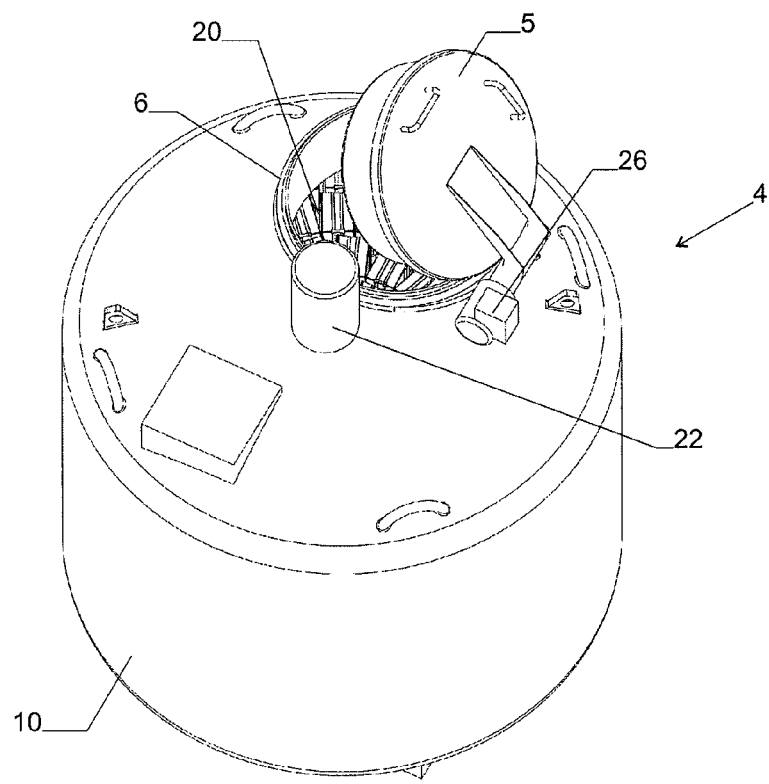
FIG. 3 A view of a Dewar flask.
Figure 4:
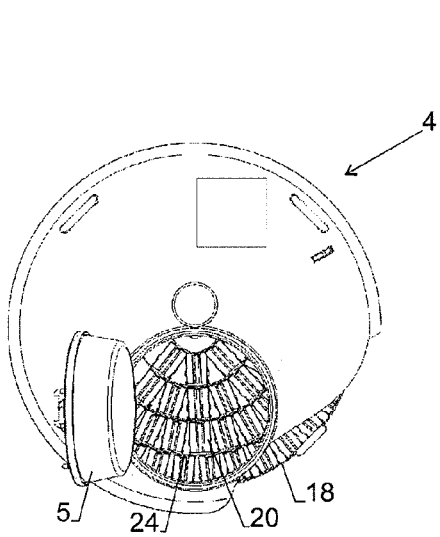
FIG. 4 The Dewar flask from FIG. 3 from above, with wall partially removed.
Figure 5:
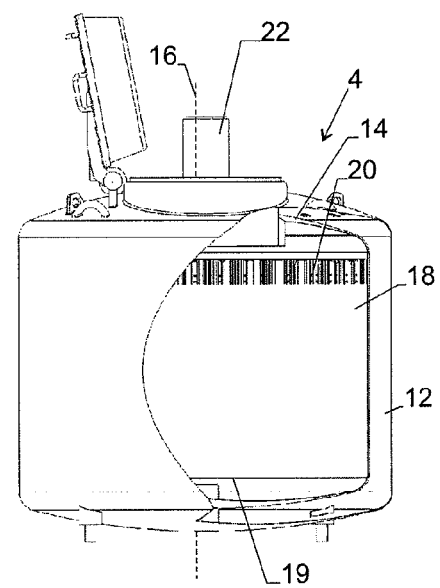
FIG. 5 The Dewar flask from FIG. 4 from the side.

Dewar Flasks:

A first embodiment of a Dewar flask 4 is shown in FIGS. 3-5. It has an essentially cylindrical housing 10, in which the above-mentioned vacuum insulation 12 is arranged. The vacuum insulation 12 surrounds an interior 14, which accommodates a carousel 18 that can be rotated about a vertical rotation axis 16. The carousel 18 bears on a base plate 19 a plurality of storage cassettes 20.

A positioning drive 22 is used to rotate the carousel 18 about the rotation axis 16 and to bring it into defined positions.

The storage cassettes 20 are arranged in several concentric circles around the rotation axis 16, radially positioned vertical walls 24 and moveable in the vertical direction.

The door 5 can be automatically opened and closed with a door drive 26. It is arranged on the top of the Dewar flask 4, and positioned and dimensioned such that when the door 5 is open each storage cassette 20, which has been rotated with the positioning drive 22 into the region of the door opening 6, can be drawn out from above. Preferably, the horizontal diameter of the door opening 6 is smaller than half the horizontal diameter of the Dewar flask 4, however, so that an excessive loss of cooling can be avoided when the door 5 is opened.

Figures 20, 21:
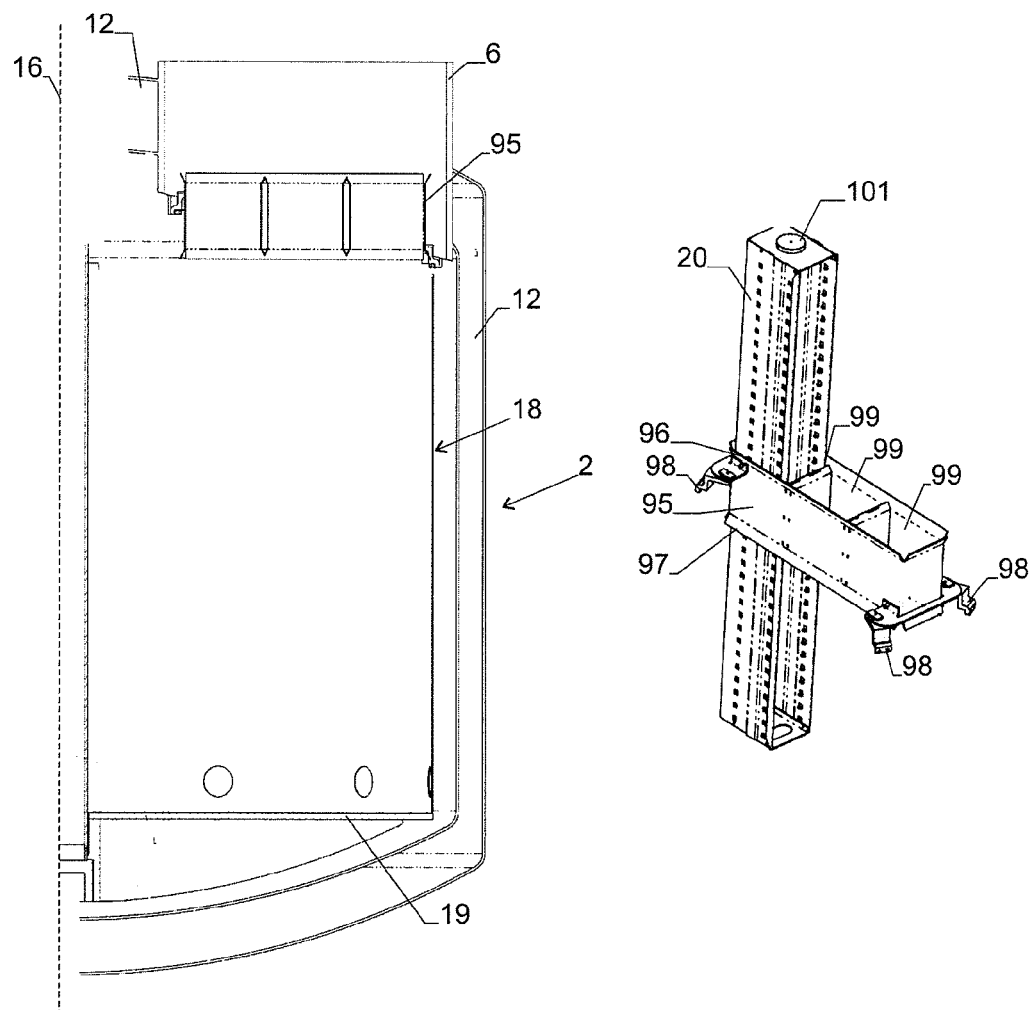
FIG. 20 A partial section through a second embodiment of a Dewar flask.
FIG. 21 A storage cassette with a second embodiment of the centering element.

A second embodiment of a Dewar flask is shown in FIG. 20. FIG. 20 shows in particular the double wall with the vacuum insulation 12 as well as the opening 6 closed by the lid 5 (not shown). A carousel 18 is again located in the interior of the Dewar flask, which carousel bears on its base plate 19 a plurality of storage cassettes (not shown).

In the embodiment according to FIG. 20, a centering element 95 is arranged in the opening 6, the function of which centering element is explained below.

Storage Cassettes:

FIGS. 6-8 show an advantageous storage cassette 20. It has two parallel, vertical side walls 30 and perpendicular thereto a vertical back wall 32. The storage cassette 20 is open opposite the back wall 32, so that the sample plates accommodated in the storage cassette 20 can be accessed. At the upper end of the storage cassette 20 a top part 34 is arranged, to which the side walls 30 and the back wall 32 as well as a handle 36 projecting upwards are attached. The handle 36 serves the picking device described below for grasping the cassette. At the lower end of the storage cassette 20, a base part 38 is arranged, to which in turn the side walls 30 and the back wall 32 are attached.

The storage cassette forms a plurality of storage sites arranged one above the other, each of which can accommodate a sample plate. They are structured such that they ensure a high mechanical precision over a very wide temperature range. Furthermore, they have centering and transport devices which render possible a high mechanical positioning accuracy and the automatic transport.

In the exemplary embodiment shown, each of the storage sites is formed by several angle brackets 40, 42. These angle brackets form support elements and project inwards from the side walls 30 (angle bracket 40) or the back wall 32 (angle bracket 42) and form lateral and back supports for the sample plates. The angle brackets 42 on the back wall 32 have on their front edge retention elements 44 (see FIG. 7) turned up i.e., bent upwards, which engage in the inserted sample plate, e.g., behind a back wall of the same, in order to thus prevent them from slipping out towards the front.

The side walls 30 of the storage cassettes 20 are bent upwards at the front and thus form bent-up regions 46, with which the storage cassette 20 is positioned laterally in the Dewar flask 4. As shown in FIG. 9, the bent-up regions 46 in each case bear laterally against a holder element 48 arranged in a stationary manner in the carousel 18. The bent-up regions 46 increase the stability of the storage cassettes. For the same reason a vertical bead 47 runs in each side wall.

As can be seen in particular from FIG. 7, the side walls 30 and the back wall 32 are formed by bent-up sections of a single piece of sheet metal. Advantageously, the top part 34 and the base part 38 are also formed by bent-up sections of the same piece of sheet metal. The angle brackets 40, 42 can also be formed by bent-up sections of the sheet metal part. The production of the storage cassette is thus simplified and the storage cassette is tough and temperature-resistant.

Predetermined bending locations 39 are provided between at least one part of the bent-up sections of the piece of sheet metal, in particular in the form of elongated holes or slots, which facilitate a locally precise bending of the piece of sheet metal during production.

Advantageously, the outline of the piece of sheet metal is cut by laser processing and the predetermined bending locations 39 are also produced with the laser in the same step so that a high relative positioning accuracy is ensured.

The storage cassette shown is suitable not only for use in the storage arrangement described here, but also for use for other purposes, e.g., in general for storage of laboratory objects (such as, e.g., microtitration plates) inside and outside climate-controlled cabinets.

Figure 22:
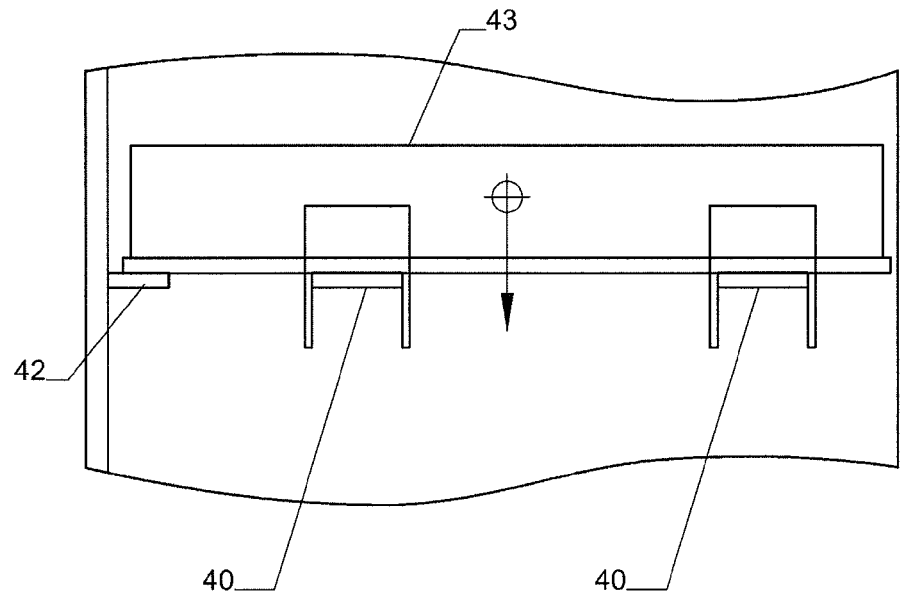
FIG. 22 A side view of a fully inserted laboratory object.

FIG. 22 shows a laboratory object in the shape of a sample plate 43, which rests on the angle brackets 40, 42. As can be seen, in each case at least two angle brackets 40 spaced apart are arranged on the side walls.

Figure 23:
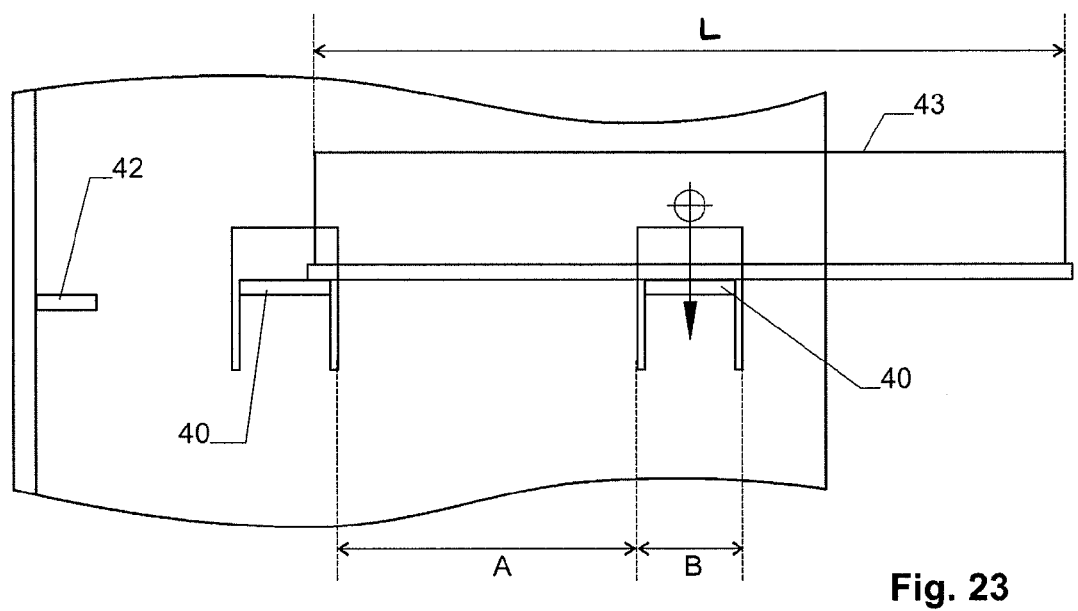
FIG. 23 A side view of a laboratory object partially inserted.

FIG. 23 shows the sample plate 43 in a position in which its center of gravity rests above the front (i.e., charging side) angle bracket 40. The distance A between the angle brackets or support elements 40 is selected such that in this position a tilting of the plate is avoided as far as possible. To this end the distance and lengths of the support elements 40 are selected such that $$|L/2-A|<B,$$

where L is the length of the laboratory plate or the storage site (in the extension direction of the scoop), A is the distance between the two support elements or angle brackets 40 arranged on the side wall and B is the length of one of the support elements, in particular the front (i.e., charging side) support element or angle bracket 40. The notation x. Designates the Amount of x.

Figure 10:
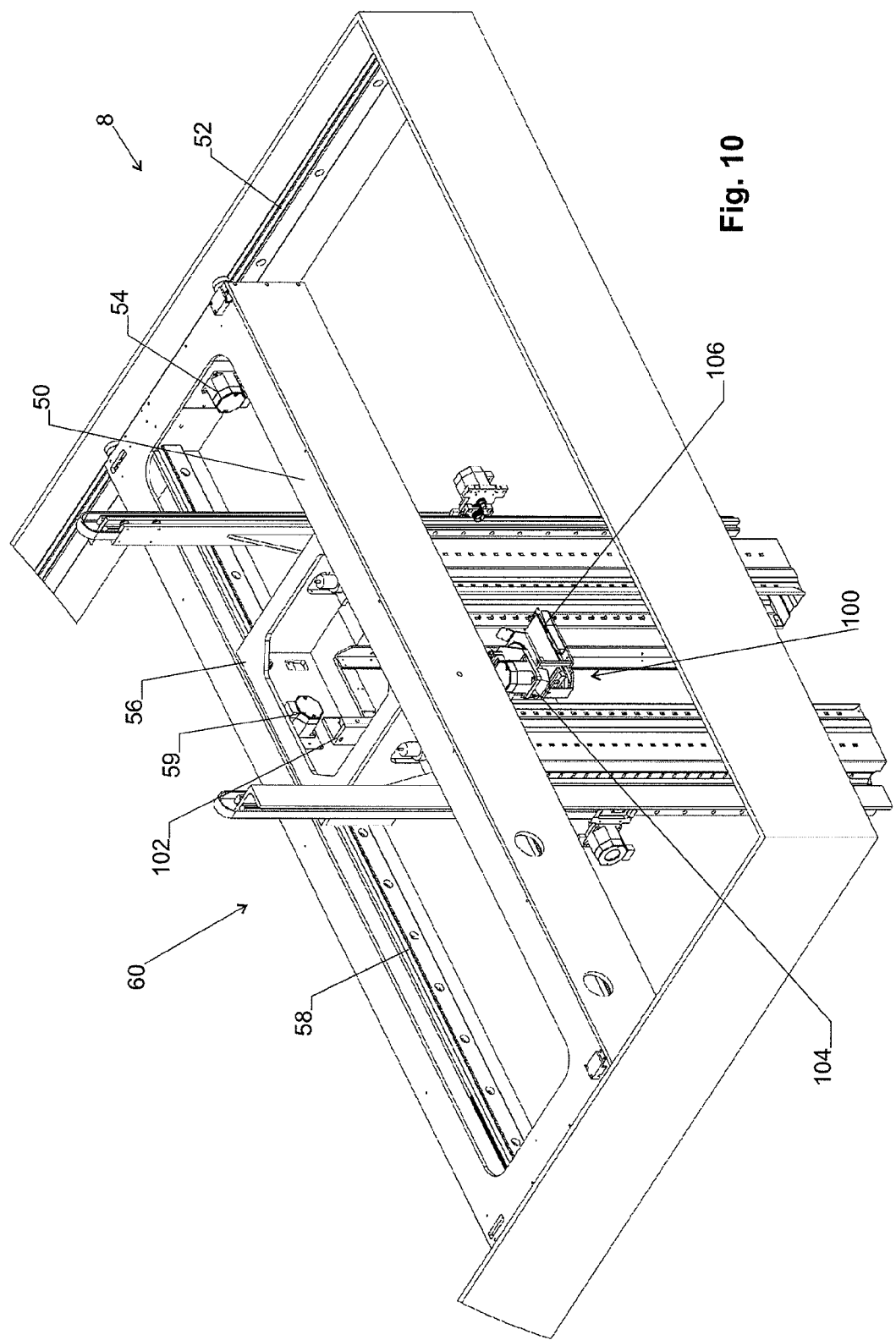
FIG. 10 A picking device.

Picking Device:

The picking device 8 is shown in more detail in FIG. 10. It has a car 50, which can be moved horizontally along a first rail 52 arranged in a stationary manner in the storage arrangement 1, for which purpose a first horizontal drive 54 is provided. A carriage 56 is arranged in the car 50, which carriage can be moved horizontally along a second rail 58, which is arranged on the car 50 perpendicular to the first rail. To this end, a second horizontal drive 59 is provided. In this manner the carriage 56 can be moved horizontally in all directions.

At least one cassette lift 60 is arranged on the carriage 56, with which cassette lift storage cassettes can be removed from the Dewar flasks 4 in the vertical direction and inserted therein again.

In the embodiment according to FIG. 10 two such cassette lifts 60 are provided. They are mounted rotated by 180° to one another. This arrangement was selected because in the embodiment according to FIGS. 1 and 2 the Dewar flasks are also arranged in two rows rotated by 180° to one another so that a correspondingly oriented cassette lift 60 is available for each row of Dewar flasks. Alternatively to this, only a single cassette lift 60 could also be provided, which can be rotated by 180° about a vertical axis. Or the Dewar flasks 4 can all be oriented identically, in which case a single non-rotatable cassette lift is sufficient.

The structure of the cassette lift is described below.

Furthermore, a handling device 100 is provided on the carriage 56. In the embodiment according to FIG. 10 this handling device 100 is arranged between the two cassette lifts 60.

The structure and the function of the handling device 100 correspond essentially to those of the handling device according to WO 02/059251.

The handling device 100 comprises a vertical guide 102, on which a handling carriage 104 is arranged in an automatically moveable manner in the vertical direction. A scoop 106 that can be extended horizontally is provided on the handling carriage 104. The scoop 106 can preferably be pivoted by at least 180° about a vertical axis so that in the embodiment according to FIG. 10 it can optionally be moved into the storage cassettes 20 of the cassette lifts 60 lying opposite one another, and there can take up or deposit a sample plate. Furthermore, it can also be pivoted in the longitudinal direction of the storage arrangement 1 in order to deposit or take up a sample plate at a transfer station 108 (see FIG. 2) arranged at the end in the storage arrangement 1.

A climate controlled cabinet 110 can be provided outside the outer housing at the location of the transfer station 108, which climate controlled cabinet is able to exchange laboratory objects or storage plates with the transfer station 108.

Figure 11:
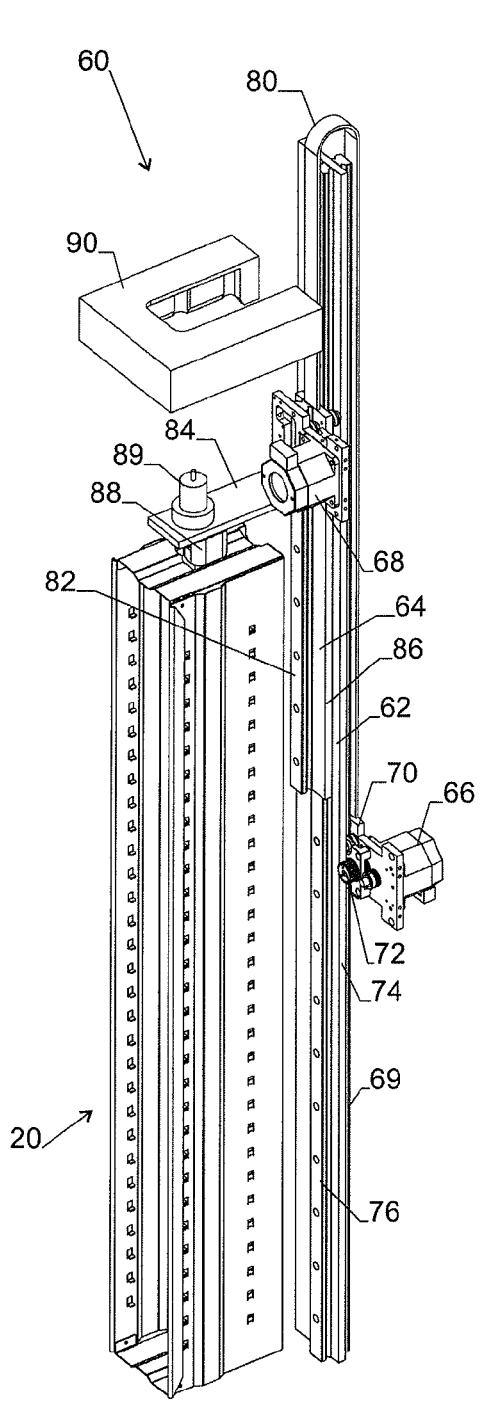
FIG. 11 A first embodiment of a cassette lift.

Cassette Lift:

FIG. 11 shows a first embodiment of a cassette lift. In this embodiment each cassette lift 60 has several telescopic sections 62, 64 that can be extended in a telescopic manner with respect to one another as well as a corresponding number of vertical drives 66, 68.

A first telescopic section 62 is attached to the carriage 56 in a stationary manner. A first vertical rail 69 is arranged on the first telescopic section 62, on which first vertical rail a first vertical drive 66 is arranged in a slidable manner. The vertical drive 66 is connected via a first guide 70 to the first vertical rail 69 and engages with a sprocket 72 in a gear rack 74 on the first telescopic section 62.

Furthermore, a second vertical rail 76 is arranged on the first telescopic section 62, to which second vertical rail the second telescopic section 64 is attached in a vertically moveable manner. It is connected via a flexible, tough, low-temperature resistant belt or a chain 80 deflected at the upper end of the first telescopic section 62 to the first vertical drive 66, so that a lowering or raising of the first vertical drive 66 causes a raising or lowering of the second telescopic section 66 by the same height relative to the first telescopic section 62. Thus the second telescopic section 64 can be extended or retracted in a telescopic manner with the first vertical drive 64.

A third vertical rail 82 is arranged on the second telescopic section 64, on which third vertical rail an arm 84 of the cassette lift 60 is supported in a vertically moveable manner. The second vertical drive 68 is designed to move the arm 84 vertically with respect to the second telescopic section 64. In the embodiment shown in FIG. 11, the second vertical drive 68 to this end engages with a sprocket in a gear rack 86 on the second telescopic section 64.

A gripper device 88 with a gripper drive 89 is arranged on the arm 84, with which the handle 36 of a storage cassette 20 can be grasped from above.

At least one centering element 90 is provided at a fixed height on the carriage 56 or on the first telescopic section 62 above the gripper device 88, which centering element forms a seat tapering upwards for accommodating a storage cassette 20, when the storage cassette is moved into its uppermost position with the cassette lift 60. Since at the same time the gripper device 88 has some clearance at the side, the centering element 90 defines the horizontal position of the raised storage cassette 20 and thus makes it possible to exactly align the storage cassette horizontally.

Figure 12:
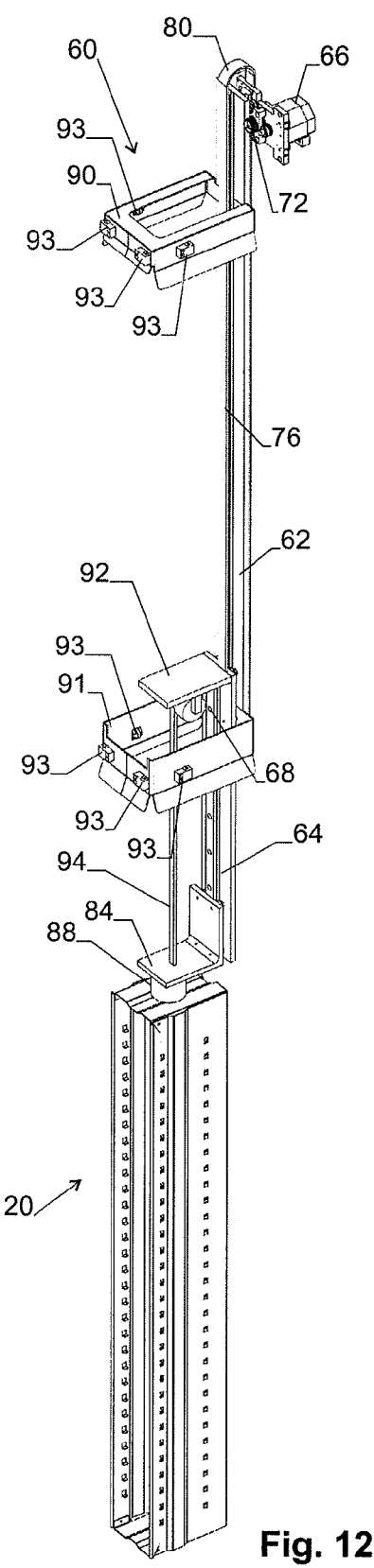
FIG. 12 A second embodiment of a cassette lift in the lowered position.
Figure 15:
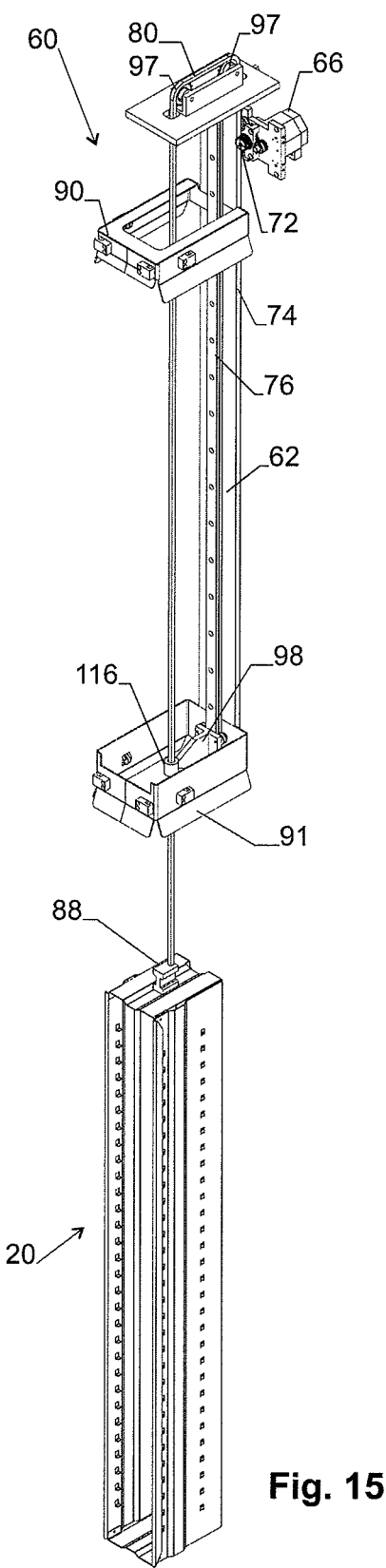
FIG. 15 A third embodiment of a cassette lift in the lowered position.
Figure 16:
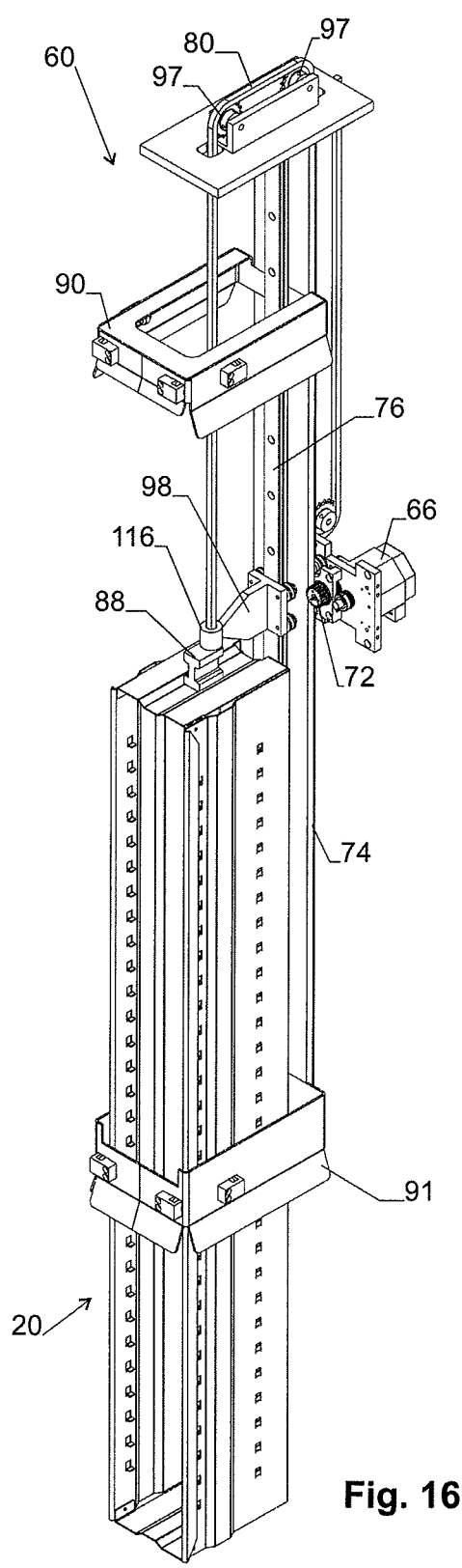
FIG. 16 The cassette lift from FIG. 15 in center position.
Figure 17:
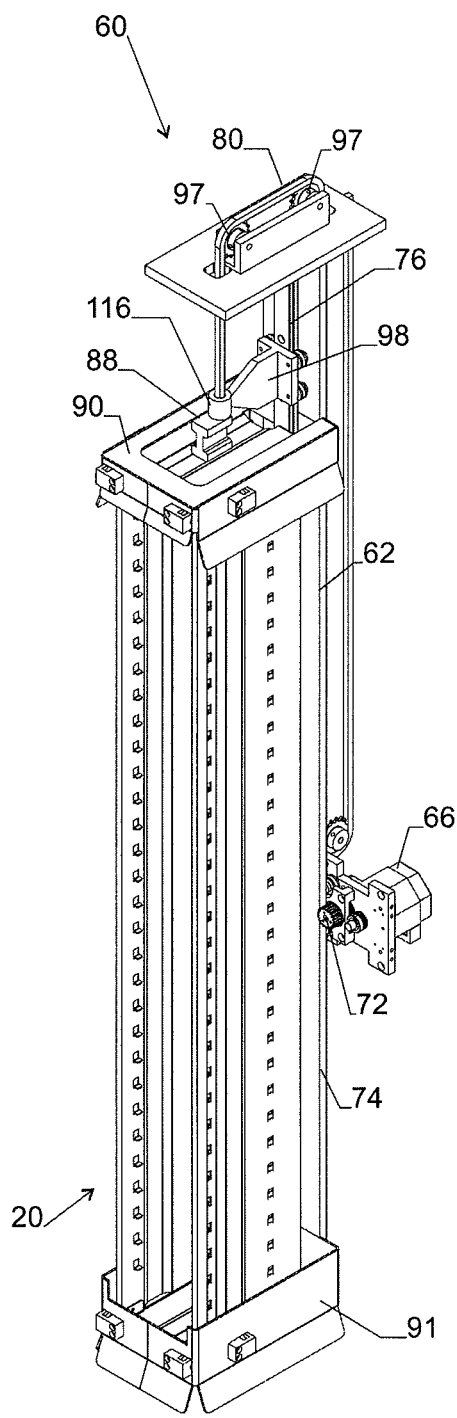
FIG. 17 The cassette lift from FIG. 15 in the raised position.

FIGS. 12-14 show a second embodiment of a cassette lift 60. It corresponds structurally to that according to FIG. 11, with the following differences:

The second vertical drive 68 is not arranged on the arm 84, but at the upper end 92 of the second telescopic section 64. It forms a reel for a chain 94, at the lower end of which the arm 84 is attached. The arm 84 can thus be raised and lowered by winding and unwinding the chain 94. This solution has the advantage that the second vertical drive can be fixedly attached to the second telescopic section 64 and does not have to be lowered so far down into the low temperature range.

Two centering elements 90, 91 spaced apart vertically from one another are provided. An upper centering element 90 is designed approximately the same as the centering element 90 of the first embodiment and again forms a seat tapering upwards for the storage cassette 20, while the lower centering element 91 forms a collar tapering upwards into which the storage cassette 20 moves when raised. When the storage cassette 20 is raised, the upper centering element 90 comes to rest in the region of the upper end of the storage cassette 20 and the lower centering element 91 comes to rest in the region of the lower end of the storage cassette 20, so that the raised storage cassette 20 is guided horizontally at both ends. In order to ensure a guidance with low friction, spring-mounted roller bearings 93 are provided on the centering elements (FIG. 12)

The gripper device 88 is embodied as an electromagnet.

FIGS. 15-18 show a third embodiment of a cassette lift 60. It corresponds structurally to that according to FIGS. 12-14, with the differences described below.

The third embodiment of the cassette lift is not based on a telescopic arrangement of elements. Instead, the chain 80 together with rollers 96, 97 forms a pulley which is used to lower the gripper device 88 into the Dewar flasks 4. To this end, the chain is deflected over at least one lower and at least one upper roller 96 and 97 respectively, cf. FIG. 18. One of the rollers, advantageously the lower roller 96, can be displaced in the vertical direction via the vertical drive 66, while the other roller and the upper end of the chain 80 are vertically stationary.

Figure 18:
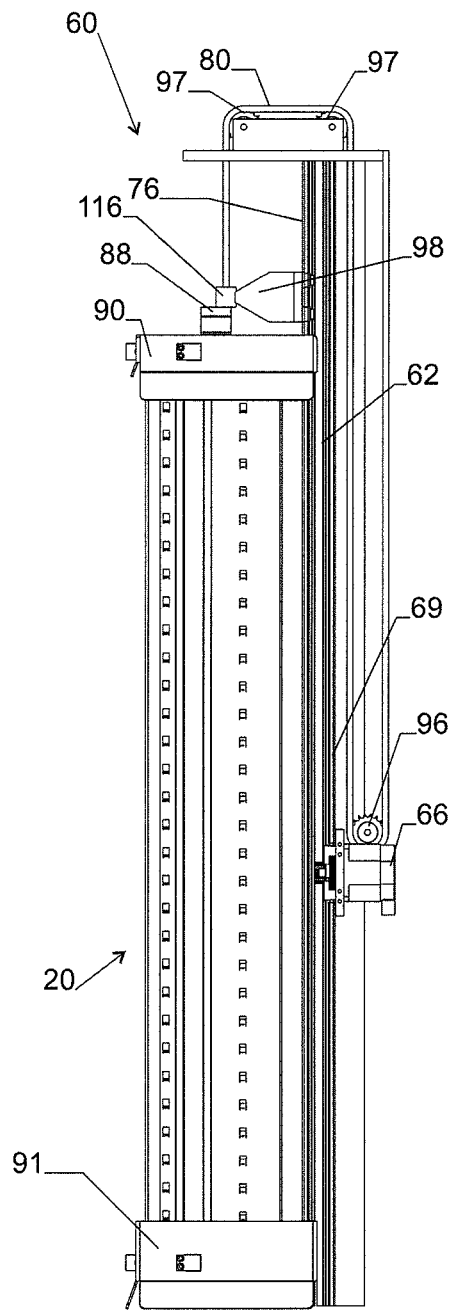
FIG. 18 A side view of the cassette lift from FIG. 17.

In the embodiment shown, the vertical drive is arranged on the first vertical rail 69 of a rail carrier 62 (FIG. 18). The rail carrier 62 corresponds to the first telescopic element 62 of the previous embodiments and is fixedly arranged on the carriage 56.

The chain 80 deflected at the upper end of the cassette lift 60 hangs vertically downwards and bears on its lower end the gripper device 88, which, as in the second embodiment of the cassette lift, is formed by an electromagnet, with which the respective storage cassette can be retained magnetically. (In FIGS. 15-18 the gripper device 88 has by way of example the same form as the handle 36 from FIG. 6, however it forms a separate element from the handle 36. When an electromagnet is used as a gripper device 88, the handle 36 can be omitted, if the storage cassette 20 can be retained at least on its lower end magnetically.)

In order to facilitate the grasping of a storage cassette 20 by magnetic force, advantageously a steel or iron plate 101 is provided at one upper end of the storage cassette 20, as is shown in FIG. 20.

In order to stabilize the chain 80 laterally somewhat, a guide element 98 is provided, which is guided on a second vertical rail 76 in a longitudinally slidable manner. The second vertical rail 76 is likewise arranged on the rail carrier 62. The guide element 98 forms a lateral guide for the chain 80, preferably an eyelet 116, through which the chain 80 runs. In the lowered position of the storage cassette 20 (cf. FIG. 16), the guide element 98 is located at a stop at the lower end of the second vertical rail 76. When the storage cassette 20 is raised, the eyelet 116 strikes the gripper 88 and is carried along, cf. FIGS. 16-18.

The embodiment according to FIGS. 15-18 has among other things the advantage that it requires only one vertical drive 66, which furthermore can be arranged relatively high on the lift and does not need to be lowered into the very cold regions of the storage arrangement.

The use of a pulley is furthermore advantageous because it makes it possible to reduce the vertical stroke of the motor and thus the installation height. However, the chain or the belt 80 does not necessarily need to be arranged in a pulley. Instead of a pulley it is also possible e.g. to roll up the belt or the chain 80 on a driven roller or reel, or to unroll it therefrom, as shown in the embodiment for the chain 94 shown in FIGS. 12-14. In this case the gripper device 88 for gripping the storage cassettes 20 can also be lowered on a chain or a belt 80 into the Dewar flasks.

Centering Element in the Dewar Flask

Additionally or alternatively to the centering elements 90 and 91, a centering element 95 can also be provided on the Dewar flask 2, as is shown in FIGS. 20 and 21. Advantageously, this centering element 95 is arranged in the opening 6. As can be seen from FIG. 21, the centering element 95 has an upper collar 96 widening upwards as well as a lower collar 97 widening downwards, which facilitate an introduction of the storage cassette 20 from above or below. It is aligned via lateral feet 98 in the opening 6 in correct position relative to the carousel 18, and it forms at least one guide opening 99, in which the storage cassette is guided horizontally when being drawn out of or inserted into the Dewar flask. A horizontal clearance, which is as low as possible, e.g., no more than 5 mm, remains between the guide opening 99 and a storage cassette 20.

In the embodiment according to FIGS. 20 and 21, the centering element has several guide openings 99, which are arranged at different distances from the rotational axis 16. The distances of the guide openings 99 from the rotational axis 16 correspond to the radii of the circles of the storage towers in the carousel 18.

Figure 19:
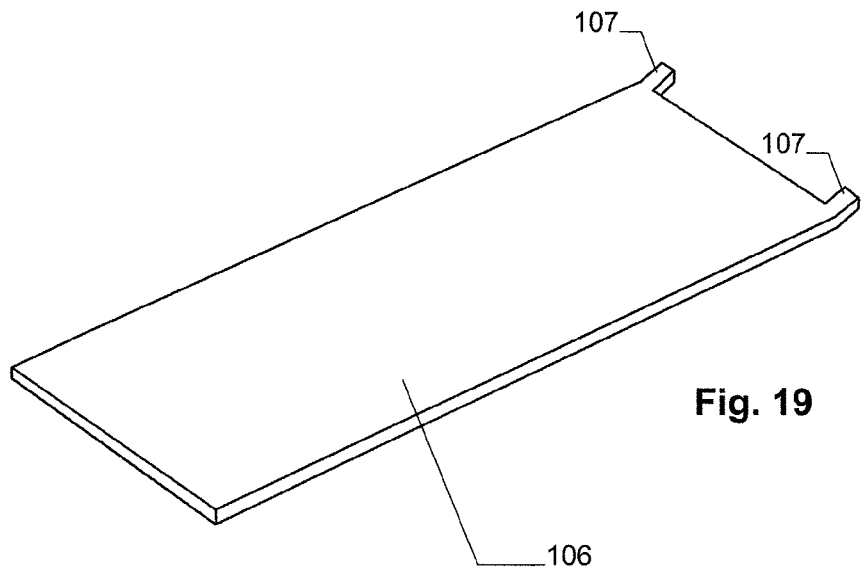
FIG. 19 The scoop from FIG. 10 in detail.

Remarks:

As shown in FIG. 19, at least one holder element 107, e.g., in the form of a finger, directed upwards, in particular directed obliquely upwards, is preferably arranged on the scoop 106 (cf. FIG. 10), namely at that end of the scoop 106 with which it is moved into the storage cassettes 20. In the embodiment according to FIG. 19, two holder elements 107 of this type are arranged spaced apart from one another. These holder elements 107 are used to secure the laboratory objects on the scoop from the rear, so that they do not fall off the scoop. In other words, the scoop thus has at least one holder element 107 with which a laboratory object to be picked up can be seized.

The back wall 32 of the storage cassettes 20 is structured such that the holder elements 107 have room to be brought from below behind a laboratory object held in the storage cassette 20. For this purpose the back wall 32, as shown in FIG. 7, is set back in two lateral regions 32*a* running vertically with respect to their central region 32*b*. In other words, a first region (central region 32*b*) of the back wall 32 forms a spacer, with respect to which at least one second region (in FIG. 7 the lateral regions 32*a*) is set back such that the holder elements 107 can be inserted behind the laboratory objects held in the storage cassette into the set back or a correspondingly recessed region, i.e., that the holder elements 107 have room behind the laboratory object held in the storage cassette. (The term "behind" thereby designates that side of the laboratory objects which faces towards the back wall 32). In the embodiment according to FIG. 19, the second region 32*a* is set back with respect to the first region 32*b*, the second region 32*a* of the back wall can also be recessed, however, as is indicated by a dashed line 23*c* in FIG. 7.

It is mentioned in the above description that the storage arrangement 1 as well as the storage cassettes 20 are used to store sample tubes. However, they are also suitable for storing samples in another form, generally suitable for storing laboratory objects. These can be, e.g., biological or chemical samples. A typical use also relates to the storage of laboratory samples in microtitration plates, in which case the sample plates are embodied as microtitration plates. It is also conceivable that, instead of the sample plates, sample holders, e.g., flasks, are used, which each hold only one sample.

While preferred embodiments of the invention are described in the present application, it should be noted that the invention is not restricted thereto and can also be carried out in another manner within the scope of the following claims.

The invention claimed is:

1. A storage cassette for laboratory objects, which forms a plurality of storage sites arranged one above the other to accommodate laboratory objects, the storage cassette comprising:
   a back wall,
   two side walls standing perpendicular to the back wall,
   wherein the side walls and the back wall are formed by sections of a single piece of sheet metal bent towards one another;
   bent angle brackets on the back wall and on the two side walls, the bent angle brackets being formed in the piece of sheet metal and being arranged as storage sites on which the laboratory objects are placed; and
   at least one of a top part and base part is arranged on a respective at least one of an upper and lower end of the storage cassette, and the at least one top and base part is formed by a bent section of the piece of sheet metal.

2. A storage cassette for laboratory objects, which forms a plurality of storage sites arranged one above the other to accommodate laboratory objects, the storage cassette comprising:
   a back wall,
   two side walls standing perpendicular to the back wall,
   wherein the side walls and the back wall are formed by sections of a single piece of sheet metal bent towards one another;
   bent angle brackets on the back wall and on the two side walls, the bent angle brackets being formed in the piece of sheet metal and being arranged as storage sites on which the laboratory objects are placed; and
   predetermined bending locations being arranged in the piece of sheet metal in the form of at least one of elongated holes and slots.

3. A storage cassette for laboratory objects, which forms a plurality of storage sites arranged one above the other to accommodate laboratory objects, the storage cassette comprising:
a back wall,
two side walls standing perpendicular to the back wall,
wherein the side walls and the back wall are formed by sections of a single piece of sheet metal bent towards one another; and
a first region of the back wall forming a spacer for the laboratory objects that delimits at least one second region of the back wall that is set back with respect to the first region.

4. A combination of a storage cassette for laboratory objects, which forms a plurality of storage sites arranged one above the other to accommodate laboratory objects and at least one laboratory object, the storage cassette comprising:
a back wall,
two side walls standing perpendicular to the back wall,
wherein the side walls and the back wall are formed by sections of a single piece of sheet metal bent towards one another; and
bent angle brackets on the back wall and on the two side walls, the bent angle brackets being formed in the piece of sheet metal and being arranged as storage sites on which the laboratory objects are placed; and
the combination further comprising at least two storage elements formed on each side wall for each storage site, the at least two storage elements being arranged such that:

$$|L/2-A|<B,$$

wherein L is a length of the laboratory object, A is a distance of the at least two support elements and B is a length of one of the support elements.

5. The storage cassette according to claim 4, wherein the at least two storage elements comprise angle brackets formed from the side walls.

6. A storage arrangement comprising:
at least one chamber; and
at least one storage cassette being arranged in the chamber, the at least one storage cassette having a back wall and two side walls standing perpendicular to the back wall, wherein the side walls and the back wall are formed by sections of a single piece of sheet metal bent towards one another;
at least one extendible scoop structured and arranged to at least one of retrieve and place a laboratory object,
wherein the at least one extendible scoop includes at least one holder element structured and arranged to seize the laboratory object from behind, and
wherein the back wall of the storage cassette comprises a first region forming a spacer for the laboratory objects and delimiting at least one second region of the back wall as a recess or set back area structured to receive the at least one holder element when retrieving or placing the laboratory object.

7. A method of forming a storage cassette for laboratory objects, the storage cassette having a plurality of storage sites arranged one above the other to accommodate laboratory objects, the method comprising:
bending a single piece of sheet metal to form a back wall and two side walls arranged perpendicular to the back wall to form a storage cassette for laboratory objects;
forming bent angle brackets from the single piece of sheet steel in the back wall and the two side walls as storage sites on which the laboratory objects are positionable; and,
bending the single piece of sheet metal to form at least one of a top part and a base part on a respective at least one of an upper and lower end of the storage cassette.

8. A method of forming a storage cassette for laboratory objects, the storage cassette having a plurality of storage sites arranged one above the other to accommodate laboratory objects, the method comprising:
bending a single piece of sheet metal to form a back wall and two side walls arranged perpendicular to the back wall to form a storage cassette for laboratory objects;
forming bent angle brackets from the single piece of sheet steel in the back wall and the two side walls as storage sites on which the laboratory objects are positionable; and
bending the back wall to form a first region as a spacer for the laboratory objects that delimits at least one second region of the back wall that is recessed or set back.

9. A method of forming a storage cassette for laboratory objects, the storage cassette having a plurality of storage sites arranged one above the other to accommodate laboratory objects, the method comprising:
bending a single piece of sheet metal to form a back wall and two side walls arranged perpendicular to the back wall to form a storage cassette for laboratory objects; and
forming bent angle brackets from the single piece of sheet steel in the back wall and the two side walls as storage sites on which the laboratory objects are positionable,
wherein at least two angle brackets are formed on each side wall to delimit each storage site, and the at least two storage elements are arranged such that:

$$|L/2-A|<B,$$

wherein L is a length of the storage site, A is a distance of the at least two support elements and B is a length of one of the support elements.

* * * * *